United States Patent [19]

Stalling

[11] Patent Number: 5,272,149
[45] Date of Patent: Dec. 21, 1993

[54] SYMPTOM CONTROLLED RECEPTOR SUBSTITUTION FOR ADDICTION WITHDRAWL

[76] Inventor: Reginald W. Stalling, 314 Golf Course Rd., Owings Mills, Md. 21117-4114

[21] Appl. No.: 878,612

[22] Filed: May 5, 1992

[51] Int. Cl.$^5$ .................... A61K 31/44; A61K 31/495
[52] U.S. Cl. .................... 514/255; 514/282; 514/812
[58] Field of Search .................... 514/255, 282, 812

[56] References Cited

U.S. PATENT DOCUMENTS

| | | | |
|---|---|---|---|
| 4,457,933 | 7/1984 | Gordon et al. | 424/260 |
| 4,464,378 | 8/1984 | Hussain | 424/260 |
| 4,661,492 | 4/1987 | Lewis et al. | 514/282 |
| 4,670,459 | 6/1987 | Sjoerdsma | 514/401 |
| 4,800,209 | 1/1989 | Sjoerdsma | 514/401 |
| 4,803,208 | 2/1989 | Pasternak | 514/282 |
| 4,935,428 | 6/1990 | Lewis | 514/282 |

OTHER PUBLICATIONS

Lever et al., "Chapter 6. Analgesics, Opioids, and Opioid Receptors", *Ann. Rep. Med. Che.*, vol. 18, pp. 51–60, (1983).
Dole et al., "Successful Treatment of 750 Criminal Addicts", *J. Am. Med. Assn.*, vol. 206, No. 12, pp. 2708–2711, Dec. 16, (1968).
Dole et al., "Methadone Treatment of Randomly Selected Criminal Addicts", *New Engl. J. Med.*, vol. 280, No. 25, pp. 1372–1375, Jun. 19, (1969).
Johnson et al., "Use of Buprenorphine in the Treatment of Opiate Addiction. I. Physiologic and Behavioral Effects During a Rapid Dose Induction", *Clin. Pharmacol. Ther.*, vol. 46, No. 3, pp. 335–343, Sep. (1989).
Charney et al., "The Combined Use of Clonidine and Naltrexone as a Rapid, Safe, and Effective Treatment of Abrupt Withdrawl From Methadone", *Am. J. Psychiatry*, vol. 143, No. 7, pp. 831–837, Jul. (1986).
Brewer et al., "Opioid Withdrawl and Naltrexone Indcution in 48-72 Hours with Minimal Drop-out, Using a Modification of the Naltrexone-Clonidine Technique", *Brit. J. of Psych.*, vol. 153, pp. 340–343. (1988).

*Primary Examiner*—Leonard Schenkman
*Attorney, Agent, or Firm*—Sandler Greenblum & Bernstein

[57] ABSTRACT

Method of treating addiction in a subject, such as a human being, by administering, to the subject, a succession of therapeutic agents. Each of these agents competes with the addictive agent for receptor binding sites, and each is administered in an amount sufficient to remove addictive agent from the subject. At least one of these therapeutic agents controls withdrawal symptoms. The method is continued until at least one of the indicated therapeutic agents fails to evoke withdrawal symptoms in the subject.

1 Claim, No Drawings

SYMPTOM CONTROLLED RECEPTOR SUBSTITUTION FOR ADDICTION WITHDRAWL

BACKGROUND OF THE INVENTION

1. FIELD OF THE INVENTION

The present invention relates to novel methods for the purpose of rapid detoxification, withdrawal and symptom management of patients addicted to target agents. In particular, the present invention relates to novel methods for the purpose of treating opioid addiction.

2. BACKGROUND OF THE INVENTION

Addiction has been defined as a behavioral pattern of drug use, characterized by overwhelming involvement with the use of a drug—i.e., compulsive use—, the securing of its supply, and a high tendency to relapse after withdrawal. The goal of treatment for addiction is to remove the addicting drug from the addicted subject's body, and to prevent the subject from reestablishing a dependence on that drug.

Unfortunately, treatment has proven to be a stubborn medical and social problem, because addiction is a recalcitrant disease. Individuals who become addicted have a great likelihood of remaining addicted, or of returning to an addicted state after a period of abstinence.

There are, in general, four basic considerations that must be addressed when treating addiction. The first is to devise a treatment that can be completed within a relatively short period of time. The second consideration is to devise a treatment wherein the symptoms associated with withdrawal of the addictive drug are controlled. The third consideration is to determine who should be admitted to a particular treatment, and how to monitor their progress on the treatment. The fourth consideration pertains to counseling of the patient and long term prevention of reoccurrence of the addictive behavior. Of these four considerations, the first two are considered amenable to pharmacological intervention.

With regard to the first consideration, the time it takes to complete the process has been, for the most part, an uncontrollable part of the treatment process. Historically, nature has simply been allowed to take its course, with the addictive agent being removed from the subject, by the body's own processes.

Recent discoveries in basic research have uncovered mechanisms that underlie the disease, and have shed light on means for affecting the period of time necessary for treating an addiction. In particular, work carried out on opioid addiction has been instrumental in this regard; specifically research has demonstrated that the addictive properties, i.e., of an addictive opioid, are the cumulative result of the binding of the drug to what is called opioid receptor sites.

The term "opioids" is a generic designation for all exogenous substances that bind specifically to any of several subspecies of opioid receptors. The term was coined after studies using analogs of opium revealed that small changes in the chemical structure of opium resulted in agents that produce agonistic, antagonistic, or a combination of agonistic and antagonistic effects in the patient, as disclosed in LEVER et al., Ann. Rep. Med. Che.. 18,51 (1983).

As also disclosed in LEVER et al., the different effects caused by the related analogues was determined to be due to their preferential binding to different opiate receptors. Further, research has shown that the analogues compete with the addictive opioid for these receptors.

The understanding that opioids could compete with the addictive agent made it possible to develop treatments that would decrease the time it took to rid the subject's body of the addictive agent. The rate is accelerated, because the competitive agent takes up binding sites.

Therefore, with the competitive agent filling opioid binding sites, there are less available binding sites for the addictive agent. Consequently, more of the addictive agent will be in the unbound form, and thus readily excreted from the subject's body.

Moreover, the discovery that analogues of the addictive agent compete with the addictive agent, for the same binding sites, made possible the development of entirely new forms of treatment. Further, treatments of addiction came to be grouped into two basic categories—i.e., competitive therapy, and "cold turkey" treatments.

Competitive therapy involves administering a therapeutic agent, i.e., a drug, that competes with the addictive agent for the available binding sites, and, therefore, increases the rate at which the addictive agent, such as an opioid, is in its unbound state. Such therapy includes all treatments wherein at least one therapeutic agent competes with the addictive agent for binding sites; these agents may or may not have other effects on the patient, but for the purposes of distinguishing between addiction therapies, the primary difference is that these agents compete for receptor sites.

"Cold turkey" treatments are those that do not employ the administration of therapeutic agents which compete with the addictive agent for binding sites. In such therapy, the addictive agent becomes unbound at a rate that is independent of any therapeutic agent being administered.

As to the second of the four basic considerations in the treatment of addiction, this involves the management of the symptoms which accompany the removal of the addictive agent from its receptor sites. Whether "cold turkey" or "competitive therapy" is used to treat the addicted subject, the withdrawal symptoms are a major concern for the patient and the long term prognosis of the disease.

Such symptoms include exaggerated autonomic stimulation, accompanied by a powerful craving for the drug. The signs and symptoms of acute withdrawal following the discontinuance of heroin, for example, include abdominal pain, nausea, vomiting, diarrhea, chills, hot flashes, restlessness, insomnia, general aches and pains, hypertension, anorexia, malaise, tachycardia, lacrimation, rhinorrhea, diaphoresis, and piloerection as well as a severe craving for the withdrawn drug; the more exaggerated the symptoms, the less likely the subject will be to use a particular treatment.

It has been found that the withdrawal symptoms differ in direct proportion to the rate at which the addictive agent is displaced from its receptor sites. The faster the addictive agent is removed from the receptor sites, the more severe the symptoms of withdrawal; on the other hand, the faster the addictive agent is removed from the receptors, the faster the subject becomes drug free, thereby leading to a shorter period of time during which the subject experiences withdrawal symptoms.

Prior to the introduction of the opioids, the most rapid method for eliminating an opiate from a subject's body was first to stop the subject from getting any more of the addictive agent, and then to allow the subject's body to rid itself of the agent. This therapy, in its purest form, provides the subject with no pharmacological assistance whatsoever.

The obvious drawback with this form of "cold turkey" treatment is that, as the concentration of addictive agent falls, the various receptors for the addictive agent become free of drug. With the addictive agent no longer stimulating the receptors, the adverse physical and psychological symptoms—collectively known as withdrawal symptoms—occur. These symptoms include exaggerated autonomic stimulation accompanied by a powerful craving for the drug. This form of "cold turkey" is characterized as a long and painful process and is associated with a high percentage of subjects who relapse to heroin abuse before completion of the treatment.

A more humane "cold turkey" approach is one which utilizes the administration of sedatives and other agents, with the goal of moderating the withdrawal symptoms. The agents used in this method of addiction treatment do not compete with the addictive agent for receptor sites.

With regard to the competitive therapies, four therapeutic modalities have been tried. The first notable variation includes treatments for addiction which utilize a substitution and maintenance protocol.

In this form of therapy, the patient's dependency is transferred from the addictive agent to a preferred therapeutic agent, and the patient is maintained on the new agent. The therapeutic agent competes with the addictive agent for binding sites, and over time replaces the addictive agent; furthermore, the therapeutic agent is an agonist of the addictive agent, in that the therapeutic agent and the addictive agent activate the same group of receptors.

In the case of heroin addiction, which is a form of opiate addiction, the heroin substitute used in maintenance therapy is most often methadone, as discussed in DOLE et al., J. Am. Med. Assn., 206, 2708 (1968) and New Engl. J. Med. 280, 1372 (1969). Another example of this approach is described in JOHNSON et al., Clin. Pharmacol. Ther. 46:, p335–343(1989); in the procedure reported therein, heroin addicted subjects were given buprenorphine instead of methadone in increasing dosages, while their endogenous heroin concentration decreased.

This technique has the benefit of reducing the painful symptoms associated with withdrawal, because the substitute produces many of the physical and psychological symptoms of the addictive opiate. Furthermore, this therapy removes the addictive agent, heroin, from the subject's body at a more rapid rate than with any of the "cold turkey" therapies.

Unfortunately, in using methadone for treatment of heroin addiction, long periods of time are required for the substitution and withdrawal programs—e.g., two to three weeks for in-patients and 8 weeks or more for out-patients, are the common periods. Furthermore, generally as to this type of therapy, the therapeutic agents which are employed are themselves highly addictive, and there is a high rate of relapse, wherein the subject slips back to heroin abuse.

The second therapeutic modality included in the "competitive therapy" category involves the use of a therapeutic agent which competitively binds to the same receptors as the addictive agent; however, in this technique, the therapeutic agent acts as an antagonist, with the target agent being the agonist. The competitive antagonist displaces the agonist, i.e., target agent, but has little addictive potential of its own, because it does not activate the receptors.

This approach has the promising effect of reducing the concentration of the target drug in the subject's body at a more rapid rate then "cold turkey" treatments. Therefore, the time required for the subject to become free of the addictive agent is greatly reduced.

Unfortunately, because the target agent is removed at an accelerated rate, this approach precipitates such exaggerated withdrawal symptoms that it has generally been limited to overdose therapy, and has rarely been used to treat addiction. Drugs that are used in this treatment include naloxone, naltrexone, and their derivatives.

The third modality of therapy that is found in the "competitive therapy" category shares some similarities with the first modality; for instance, the therapeutic agent competitively binds to the same receptors as the addictive agent and also acts as an agonist. However, this therapy differs from the substitution modality, with regard to its intended object.

Specifically, for this third modality, the goal is for the patient to become free of any addiction; the technique employed, to achieve this end, is to slowly decrease the dosage of the substitute drug to nothing. Unfortunately, there is no drug that has been found as yet which fits this modality, without also producing a long period of withdrawal symptoms.

The final therapy that has been under investigation to withdraw patients from opiate addiction is the use of a combination therapy including elements of the "cold turkey" and "competitive therapy" categories described above. With regard to opiate addiction, the rapid withdrawal of the addictive opiate using a combination opiate based and non-opiate based treatment has been carried out with mixed results.

For example, CHARNEY et al. Am.J. Psychiatry 143:7,831–837 (1986), discusses a protocol wherein methadone addicted subjects were withdrawn from the drug over a 4–5 day period; the subjects were given clonidine hydrochloride, which is an imidazole antihypertensive and a non-opioid, to reduce opiate withdrawal signs and symptoms. In addition, the subjects were given naltrexone as an opiate antagonist.

CHARNEY et al. discloses that, although the clonidine reduced the withdrawal symptoms, it did not eliminate them. Furthermore, clonidine was found to have contraindications associated with hypotension.

Various additional treatments are known in the art. Examples of these are discussed below.

For instance, BREWER et al., Brit. J. of Psych. (1988), 153, 340–343, discloses a variation on the method of CHARNEY et al., wherein a sedative—i.e., diazepam—is used with the indicated naltrexone-clonidine method, to withdraw opiate addicted patients. The technique discussed in BREWER et al. also utilizes increased dosages of naltrexone and clonidine; the result of such treatment is stated to be a reduction, in the time for withdrawal, to 2–3 days.

It is further disclosed, in BREWER et al, that the drugs were given simultaneously, except for an initial period, when clonidine was administered alone. The stated purpose for this procedure is to prepare the patient for the first dose of naltrexone.

Yet further in BREWER et al., it is hypothesized that the naltrexone rapidly normalizes the number and sensitivity of opiate receptors, and reverses opiate-induced central noradrenergic hypersensitivity. Contraindications associated with clonidine are indicated rarely to have occurred, to have responded quickly to a reduction in the clonidine dose, and to have been of little clinical significance.

SJOERDSMA U.S. Pat. No. '459, U.S. Pat. No. 4,670,459, and SJOERDSMA U.S. Pat. No. '209, U.S. Pat. No. 4,800,209, disclose use of a combined treatment, but with the use of the competitive agent limited to the role of prevention after the subject had gone through withdrawal. These patents describe the use of lofexidine for the treatment of the symptoms caused by withdrawal from an addictive drug, e.g., methadone, by premenstrual tension, and by peri-menopausal flushing. Both oral and parenteral administration of the drug are disclosed; specifically, the treatment involves a 10 day course of lofexidine, followed by the administration of naltrexone.

In LEWIS U.S. Pat. No. '428, U.S. Pat. No. 4,935,428, a treatment for opiate dependence is disclosed, wherein buprenorphine and naltrexone are employed. Specifically, the buprenorphine is employed as a substitute for the opiate agent to which the patient is addicted.

According to LEWIS U.S. Pat. No. '428, the problem with using buprenorphine is that, in a soluble form, it has a high abuse potential of its own. LEWIS U.S. Pat. No. '428 further indicates that the useful sublingual dose range of buprenorphine for addict treatment—i.e., 2 mg to 8 mg—is about 10 times higher than the analgesic dose range, and when injected, is potentially equivalent to 60–240 mg morphine or 30–120 mg heroin; as such, this drug will have a significant value to street addicts.

The means for addressing this problem is stated to be the addition, to the buprenorphine dose, of a dose of naltrexone which is sufficient to precipitate abstinence. The specific treatment disclosed is a daily sublingual dose of 2 to 8 mg of buprenorphine for 1 to 4 weeks, followed by, as maintenance treatment, the daily simultaneous administration, in sublingual form, of 2 to 8 mg buprenorphine and an amount of naltrexone wherein the weights of naltrexone and buprenorphine are within the ratio of 1:4 to 1:1.

The treatment for withdrawing the subject is indicated to be sublingual administration, of a single agonist-antagonist, over a 1–4 week period. This is followed by a maintenance period, wherein the subject is sublingually administered a simultaneous combination of an agonist-antagonist and an antagonist.

LEWIS, et al. U.S. Pat. No. '492, U.S. Pat. No. 4,661,492, discloses an analgesic composition in parenteral or sublingual unit dosage form, comprising an active dose of buprenorphine, and an amount of naltrexone sufficient to prove aversive to a narcotic addict by parenteral administration, but insufficient to compromise the analgesic action of the buprenorphine. The dose of buprenorphine in the parenteral form is from about 0.3 mg to about 0.6 mg, and in the sublingual form, from about 0.1 mg to about 0.4 mg; the relative weights of naltrexone and buprenorphine are within the ratio of 1:12 to 1:3 for the parenteral form, and within the ratio of 1:4 to 1:1 for the sublingual form.

This patent primarily addresses the issue of providing a method of administering buprenorphine, in a dosage formulation that would render it with a low abuse level, while sustaining its analgesic properties. There is no disclosure pertaining to the use, of any of the agents discussed in the patent, for addiction withdrawal purposes.

GORDON et al., U.S. Pat. No. 4,457,933, discloses a method of decreasing both the oral and parenteral abuse potential of strong analgetic agents such as oxycodone, propoxyphene and pentazocine, by combining an analgesic dose of analgetic agents, with naloxone, in specific, relatively narrow ranges. Oxycodone-naloxone compositions having a ratio of 2.5–5:1 parts by weight, and pentazocine-naloxone compositions having a ratio of 16–50:1 parts by weight, are indicated to be preferred.

The stated goal, for such combination of agents, is to reduce analgetic agent abuse; such reduction in abuse will accordingly enable certain strong analgetic agents, in combination with naloxone, to be subject to a lower schedule of narcotic control than required for the analgetic agent alone, thereby permitting greater use thereof. GORDON et al. further discloses that, within certain narrow ranges, the combination of the powerful analgetic and naloxone produced the effect of the analgesic, without the addictive side effects.

HUSSAIN, U.S. Pat. No. 4,464,378, discloses administration of narcotic antagonists, narcotic analgesics, and related compounds, and dosage forms containing those compounds which are adapted for nasal administration. The patent discloses a nasal preparation for each of naloxone, naltrexone, and buprenorphine but not using any of them in combination, or together in the same treatment; there is further no disclosure pertaining to withdrawal from opioid addiction.

PASTERNAK, U.S. Pat. No. 4,803,208, discusses the 14-hydroxydihydromorphinone hydrazones (naloxazone, oxymorphazone and naltrexazone) and their irreversible binding to opiate receptors; such activity is indicated to result probably by the formation of these compounds' azines. The patent discloses naloxone and naltrexone in terms of their azine derivative, and indicates that the hydrazone and azine derivatives of these compounds are not as capable of displacing agents from opioid receptors as the parent compound.

PASTERNAK further discusses the use of the antagonists naloxonazone and naltrexonazine as blockers of morphine, and other opiates, in maintenance programs from opioid abuse. PASTERNAK discloses that the benefit of the dihydromorphinone compounds, as agents for opiate maintenance programs, is due to their prolonged action—i.e., in the order of days—compared to the duration of currently available drugs—i.e., in the order of only a few hours.

SUMMARY OF THE INVENTION

This invention relates to a method for the treatment of addiction in a subject, by reducing the amount of the target addictive agent in the subject. This method comprises the successive administration of a plurality of therapeutic agents, each in an amount effective to reduce the physiological level of the target agent in the subject.

In the method of this invention, each of the indicated plurality of therapeutic agents competes, with the target agent, for binding sites. Also, at least one of the plurality of therapeutic agents controls withdrawal suffered by the subject, as a result of dropping physiological levels of the target agent.

Preferably, following the method of the invention, the administration of the plurality of therapeutic agents continues at least until one of the therapeutic agents fails to evoke withdrawal symptoms in the subject.

In a preferred embodiment, of the method of the invention, at least two of the indicated plurality of therapeutic agents have different half lives. Also as a preferred embodiment, at least two of such agents have different binding site affinities.

In the latter of the two preferred embodiments discussed above—i.e., wherein at least two of the therapeutic agents have different binding site affinities—it is particularly preferred that at least one, of the plurality of therapeutic agents, comprises an agonist-antagonist. Preferably, this agonist-antagonist comprises a selective agonist-antagonist, such as an opioid agonist-antagonist. Buprenorphine is a suitable such opioid agonist-antagonist.

Further as to the preferred embodiment, wherein at least two of the plurality of therapeutic agents have different binding site affinities, at least one, of the plurality of therapeutic agents, comprises an antagonist— preferably, a selective antagonist. Suitable selective antagonists include the opioid antagonists, two such opioid antagonists being naloxone and naltrexone.

In addition to administration of the plurality of therapeutic agents, as previously discussed, the method of the invention may also include administration of a noncompetitive agent, i.e., an agent which does not compete with the target agent for binding sites. Such noncompetitive agent is administered in an amount which is effective to control the subject's withdrawal symptoms.

Preferably, the noncompetitive agent comprises a member selected from the group consisting of the autonomic nervous system blockers. Hydroxyzine is one suitable such blocker.

The method of the invention, as previously discussed, preferably incorporates three phases of treatment. These are the first induction phase, the elimination phase, and the second induction phase.

The first induction phase comprises the administration, in succession, of a plurality of therapeutic agents, each in an amount effective to reduce physiological levels of addictive agent in the subject. Moreover, each of the plurality of therapeutic agents competes with the target agent for binding sites, and at least one of the plurality of therapeutic agents controls withdrawal symptoms in the subject; such withdrawal symptoms result from reduction of physiological levels of the target agent in the subject.

This first induction phase further comprises administering, to the subject, a noncompetitive agent, in an amount effective to control such withdrawal symptoms. Moreover, the noncompetitive agent accomplishes this goal without competing with the target agent for binding sites.

The elimination phase comprises administering, in succession, to the subject, a plurality of therapeutic agents, each in an amount effective to reduce physiological levels of addictive agent in the subject. More particularly, each of such plurality of therapeutic agents competes with the target agent for binding sites; also, at least one of the plurality of therapeutic agents controls the withdrawal symptoms which result, in the subject, from the reduction of physiological levels of the target agent. Furthermore, the administration of the last therapeutic agent in this succession substantially eliminates the target agent from the subject.

The second induction phase comprises administering in succession, to the subject, a plurality of therapeutic agents, each effective for competing with the target agent for binding sites. Further, at least one of this plurality of therapeutic agents controls the indicated withdrawal symptoms. Moreover, the administration in succession of the plurality of therapeutic agents continue until at least one of the therapeutic agents fails to evoke withdrawal symptoms in the subject.

Preferably, a base line analysis, of the levels of target agent, is conducted prior to the first induction phase. More preferably, this base line analysis comprises urinalysis.

It is further preferred, in this embodiment of the invention, to administer a hydration medium to the subject, prior to the indicated first induction phase; this medium is administered in an amount effective to hydrate the subject. Preferred such hydration medium comprises 5% dextrose and water, normal saline solution, lactate ringer's solution or sterile water.

It is preferred, in this embodiment, that the noncompetitive agent comprise an autonomic nervous system blocker, such as an antihistamine. Hydroxyzine is a suitable such antihistamine.

It is preferred that at least one of the plurality of therapeutic agents administered in the first induction phase, and also at least one of the plurality of therapeutic agents administered in the second induction phase, comprise an antagonist of the target agent. An appropriate such antagonist is naloxone.

Also as a preferred embodiment, at least one of the plurality of therapeutic agents administered in the first induction phase, and at least one of the plurality of therapeutic agents administered in the elimination phase, comprises an agonist-antagonist. Buprenorphine is an appropriate such agonist-antagonist.

Periodic analysis, of the physiological levels of the target, may be conducted during the elimination phase. Preferentially, such periodic analysis comprises urinalysis.

Prior to the first induction phase the subject may be administered a hydration medium, in an amount effective to hydrate the subject. Preferably the hydration medium comprises 5% dextrose and water, normal saline solution, lactate ringer's solution or sterile water.

It is also appropriate to conduct periodic analysis, of the physiological levels of the target agent, during the second induction phase. Here also, such periodic analysis preferably comprises urinalysis.

The second induction phase may further comprise the administration of an autonomic nervous system blocker to the subject. Suitable autonomic nervous system blockers are the antihistamines, such as hydroxyzine.

Further, as to the second induction phase, it is preferred that at least one of the plurality of therapeutic agents administered therein comprise an antagonist of the target agent; a suitable such antagonist comprises naltrexone. It is also preferred, with respect to the second induction phase, that at least one of said plurality of therapeutic agents provides the ability to substantiate the elimination of the target agent from the subject; here also, naltrexone is appropriate.

The method of the invention is particularly suitable for treating opioid based target agents. These include heroin, morphine, and demerol.

A preferred embodiment of the method of the invention, for treating addiction of a subject to an opioid based target agent, comprises the following steps:

(1) administering a hydration medium to the subject, in an amount effective to hydrate the subject;

(2) administering an autonomic nervous system blocker to the subject, in an amount effective to block withdrawal symptoms in the autonomic nervous system of the subject;

(3) after initiation of blocking of the withdrawal symptoms, administering a short acting competitive antagonist to the subject, in an amount effective to substantially eliminate the opioid based target agent from the subject;

(4) after the subject experiences withdrawal symptoms, administering an amount of an agonist-antagonist to the subject, in an amount effective to substantially eliminate the withdrawal symptoms from the subject;

(5) conducting urinalysis, for the purpose of determining physiological levels of opioid based target agent in the subject;

(6) repeating steps (4) and (5) in succession, until the urinalysis indicates substantial elimination of the opioid based target agent from the subject;

(7) repeating steps (1) and (2), in succession;

(8) after initiation of blocking of the withdrawal symptoms, administering a short acting competitive antagonist to the subject, in an amount effective to displace any other competitive agent from the opioid binding sites;

(9) after cession of symptoms of discomfort in the subject, administering a long acting competitive antagonist of the opioid based target agent to the subject, in an amount effective to displace the short acting competitive antagonist;

(10) administering an opioid based agonist-antagonist to the subject, in an amount sufficient to effect a sense of well being in the subject;

(11) repeating steps (9) and (10) in succession, and, in each repetition of step (9), administering progressively greater amounts of the long acting competitive antagonist to the subject; and

(12) concluding step (11) with a repetition of step (9), wherein the long acting competitive antagonist fails to evoke withdrawal symptoms in the subject.

In a further preferred embodiment of the invention the method of addiction withdrawal can be practiced as follows.

A particularly preferred embodiment of the method of the invention, for treating addiction of a subject to heroin, comprises the following steps:

(1) conducting urinalysis of the subject's urine, to determine base line physiological level of heroin in the subject;

(2) administering approximately 1000 cc. of a medium, comprising 5% dextrose and water, normal saline solution, lactated ringer's solution, or sterile water, to the subject;

(3) administering approximately 50-100 mg. hydroxyzine, and further separately administering another approximately 50-100 mg. hydroxyzine, to the subject;

(4) after approximately 20-40 minutes, administering approximately 0.2-2.0 mg. naloxone to said subject;

(5) after approximately 20-30 minutes, administering approximately 0.3-2.1 mg. buprenorphine to the subject;

(6) after approximately 8-12 hours, administering approximately 0.3-2.1 mg buprenorphine to the subject;

(7) repeating step (6) approximately 6-9 times, during a period of approximately 72 hours;

(8) conducting urinalysis of the subject's urine, every 12 hours during step (7), to determine the physiological level of heroin in the subject; (9) administering approximately 1000 cc. of a medium comprising 5% dextrose and water, normal saline solution, lactated ringer's solution, or sterile water to the subject; (10) administering approximately 100-200 mg of hydroxyzine to the subject; (11) after approximately 20-40 minutes, administering approximately 0.2-2.0 mg. naloxone to the subject; (12) after approximately 2 hours, administering 12.5 mg of naltrexone to said subject; (13) after approximately 2-3 minutes, administering approximately 0.3-0.6 mg. of buprenorphine to the subject; (14) after approximately 12 hours, repeating steps (12) and (13); (15) after approximately 12 hours, administering approximately 25 mg. of naltrexone to the subject; (16) repeating step (13); and (17) after approximately 12 hours, administering approximately 50 mg. of naltrexone to the subject.

DETAILED DESCRIPTION OF THE INVENTION

Herein, "pharmacological agent" is used to describe substances that are administered to a subject for the purpose of inducing a biochemical change in the subject. The term "therapeutic agent," as used herein, refers to a substance administered, in the process of this present invention, in furtherance of achieving the purpose of this present invention—i.e., the treatment of addiction. It is understood that both addictive agents, as discussed below, and nonaddictive agents, can be therapeutic agents, for the purpose of this present invention.

The term "addictive agent," as used herein, refers to any substance that is capable of inducing addiction in a subject.

The term "competitive agent," as used herein, refers to a pharmacological agent that shares a binding site with another pharmacological agent.

The term "competitive therapeutic agent," as used herein, refers to a therapeutic agent that is a competitive agent.

The term "target agent," as used herein, refers to any addictive agent present in the subject, the removal of such agent being the purpose of this present invention. Target agents include, but are not limited to, heroin, morphine, demerol, codeine, nicotine, and cocaine.

The term "physiological level," as used herein, refers to the concentration of any substance in a subject, at any point in time, that produces a medically or individually perceivable effect on the subject.

The term "withdrawal symptom," as used herein, refers to any symptom that results from the reduction in physiological levels of an addictive agent.

The term "half life," as used herein, refers to the period of time required to reduce the physiological level of a pharmacological agent by one half.

The term "autonomic nervous system blocker," as used herein, refers to any pharmacological agent that has, as its primary function, the property of interfering with the functioning of the autonomic nervous system by binding to nonopioid binding sites.

The term "base line," as used herein, refers to the initial value for the physiological level of a target agent.

The term "elimination," as used herein, refers to the process by which a pharmacological agent is removed from the body or by which a physiological level is reduced.

The term "receptor," as used herein, refers to a molecule that binds to a specific portion of a pharmacological agent.

The term "binding site," as used herein, refers to the location on a receptor where the therapeutic agent combines chemically with the receptor.

The term "nonaddictive agent," as used herein, refers to any substance that generally does not induce addiction in a subject.

The term "subject," as used herein, refers to an organism, such as a human being, that is addicted to a target agent.

The term "high affinity competitive antagonist," as used herein, refers to any substance that has an affinity that is higher than the target agent.

The term "low affinity competitive antagonist," as used herein, refers to any substance that has an affinity that is lower than the target agent.

The term "selective antagonist," as used herein, refers to an antagonist that functions against a particular class of target agents. For instance, a selective antagonist which is selective against nicotinamide based addictive agents, is selective for nicotine based agents; a selective antagonist for opioid based agents is selective for opioid based agents.

The term "selective agonist-antagonist," as used herein, refers to an agonist-antagonist that functions in a particular class of target agents in a similar manner.

The term "short acting competitive antagonist," as used herein, refers to a competitive antagonist having a half life which is short enough to enable such antagonist to displace the addictive agent from the receptors, but is not long enough to significantly prevent the rebinding of the addictive agent to the receptor sites.

The term "long acting competitive antagonist," as used herein, refers to a competitive antagonist having a half life which is long enough to provide the displacement of the addictive agent from the receptors, and to prevent reattachment of the addictive agent to the receptor sites.

It has been discovered that combinations of certain competitive therapeutic agents, when administered in succession, and in pharmaceutically effective amounts, to subjects addicted to target agents, unexpectedly succeed in reducing the physiological level of the target agent in said addicted subjects, while simultaneously controlling withdrawal symptoms, and preventing re-addiction.

As an embodiment of the present invention, a treatment for addiction has now been discovered comprising the administration of a succession of therapeutic agents that compete with the target agent for binding sites, with the surprising result that the treatment can be designed to produce a minimum of withdrawal symptoms, and to prevent re-addiction. The present invention provides these unexpected results for the treatment of addiction by integrating two distinct methods.

The first of these methods uses a succession of therapeutic agents, administered to compete with the target agent for binding sites. This method results in the reduction of the physiological level of bound target agent. The second method uses therapeutic agents to control the withdrawal symptoms, associated with the reduction in the physiological level of the bound target agent, caused by the first method.

The first method of using a succession of therapeutic agents to treat addiction—i.e. using this succession to compete with the target agent for binding sites—has the effect of causing a shift in the binding equilibrium of the target agent, and an increase in the percentage of unbound target agent. As the target agent is eliminated primarily in the unbound form, this competitive method leads to the reduction of the physiological level of target agent.

The two characteristics of competition that determine the extent of elimination of target agent are as follows: firstly, the difference in affinity between the various therapeutic agents and the target agent for the binding sites; secondly, the half life of the therapeutic agent.

As to the first of these characteristics, affinity refers to the degree of permanence of the bond between the pharmacological agent and the binding site. An agent with a high affinity for a binding site will bind with a greater degree of permanence to the binding site, and remain bound for a longer period of time, than will an agent with a lower affinity for the binding site. Furthermore, if two agents compete for the same binding site, the agent with the higher affinity will bind preferentially over the agent with the lower affinity.

Thus, in one embodiment of the present invention, i.e., the treatment of opioid addiction, the therapeutic agents are chosen from the group of agents that compete with opioids for binding sites. These agents are themselves opioids; particular opioid therapeutic agents such as buprenorphine, naltrexone, and naloxone are considered on the basis of their affinity for the opioid binding sites.

Buprenorphine, for example, exhibits moderate affinity for opioid receptors; on the other hand, naltrexone and naloxone have high affinity for the opioid receptors. Therefore, given an equal amount of bound target agent prior to treatment with either opioid, a treatment with the same dosage of therapeutic opioid will result in the high affinity opioid, such as naltrexone or naloxone, causing more of the addictive opioid to be in the unbound form.

The second characteristic of competition that determines the degree of elimination, and therefore the extent of reduction of physiological level of target agent, is the half life of the therapeutic agent. Specifically, the half life of a pharmacological agent is a measure of the time it is effective in the body.

Further as to this matter, the longer the half life, the longer a particular dose of the pharmacological agent is effective; moreover, a pharmacological agent that has a short half life produces its effect for a short period of time. Therefore, a competitive agent with a short half life, herein referred to as a short acting competitive agent, may reduce the physiological level of target agent in the bound form, but the effect may be of such a temporary nature that some of the target agent may be able to rebind to receptors before being eliminated. Moreover, a competitive agent with a long half life, herein referred to as a long acting competitive agent, may reduce the physiological level of target agent in the bound form; however, the effect is long enough to enable the substantial elimination of the target agent.

Thus, in applying this second consideration to the treatment of opioid addiction, in the process of the present invention, the therapeutic agents can be classified as being long acting—as having a long half life—or as being short acting—i.e., as having a short half life. Naloxone, for example, is a short acting competitive antagonist, has a short half life and is eliminated from the body at a rapid rate. On the other hand, Naltrexone is a long acting competitive antagonist, has a long half life and is eliminated only slowly.

In the context of this application, it is understood that the antagonists, including the short acting and long acting competitive antagonists, as discussed above, exhibit, as one of their functions, the property of blocking the receptor to which they are bound.

Therefore, combining the two indicated characteristics—i.e., affinity and half life,—it is possible to categorize the competitive properties of each of the competitive agents useful to reduce the physiological level of target agent. For example, naltrexone has both a long half life and a high affinity for the opioid receptors. Naloxone, on the other hand has a short half life and a high affinity for the opioid receptor.

The second method,—i.e., integrated with the first method, as discussed above, to provide the presently claimed treatment for addiction—controls the withdrawal symptoms associated with the reduction in the physiological level of bound target agent. The withdrawal symptoms are controlled using two approaches, as discussed below.

Specifically, the first approach separates and uses those competitive agents which also affect—particularly, which minimize— the withdrawal symptoms that accompany the reduction in physiological level of the target agent. In contrast, the second approach uses the administration of noncompetitive agents to control the withdrawal symptoms.

In the first approach, some of the therapeutic agents selected to compete with the target agent for binding sites also exhibit agonist properties. In other words, not only do these therapeutic agents compete for binding sites, but they also mimic certain attributes of the target agent. This activity is thought to be caused by the therapeutic agent binding to and activating the same receptors that the target agent binds to and activates.

The second approach, for managing the symptoms associated with the reducing the physiological level of target agent in a subject, is to administer therapeutic agents that are unrelated to the target agent. These unrelated agents do not compete with the target agent for binding sites, but, in any event, control withdrawal symptoms.

This second method is necessary because, during the withdrawal process, some of the competitive therapeutic agents are selected primarily for their ability to compete with the target agent. This selection is made in order to rapidly reduce the physiological level of bound target agent, and consequently rapidly eliminate the target agent.

In relation to opioid addiction, agents that have a high affinity for the opiate receptors do not necessarily exhibit agonistic properties. Therefore, in order to control the withdrawal symptoms, an additional therapeutic agent is administered that will control symptoms without binding to opiate receptors.

In regard to the present invention, the noncompetitive agent is an autonomic nervous system blocker. In particular, the agent blocks the withdrawal symptoms, associated with the reduction in the physiological level of the target agent, that are caused by the autonomic nervous system.

Another aspect of this invention is that the method for reducing the physiological level of target agent, in said subject, comprises administering in succession, to said subject, a plurality of therapeutic agents. More specifically, the therapeutic agents are administered in succession for the dual purpose of reducing the physiological level of target agent, and controlling the withdrawal symptoms associated with said reduction in target agent.

It is preferred that, in the practice of this present invention, the period of time during which the plurality of therapeutic agents are administered in succession, is divided into three sets of sequentially timed events. They are termed the first induction phase, the elimination phase, and the second induction phase.

The first induction phase involves the initiation of the method of reducing the physiological level of target agent in the subject. This is followed by the elimination phase, which involves a period during which the subject is maintained on a successive administration of a plurality of therapeutic agents that promote the continuous reduction, and final elimination, of the physiological level of the target agent. The last phase—i.e., the second induction phase—involves administering in succession, to said subject, a plurality of therapeutic agents, at least until one of these agents confirms that the subject is no longer addicted to the addictive agent.

This induction phase can thusly be continued at least until one of the indicated therapeutic agents fails to evoke withdrawal symptoms in the subject. Such failure to evoke withdrawal symptoms can serve to confirm that the subject is, accordingly, no longer addicted to the addictive agent.

In a further preferred embodiment of the invention, the first induction phase involves the establishment of a base line level of the target agent and the proper hydration of the patient. This is followed by the administration of a noncompetitive agent in an amount effective to control withdrawal symptoms.

In this regard, the major signs and symptoms of withdrawal are connected to the autonomic nervous system. The signs and symptoms of acute withdrawal following the discontinuance of heroin, for example, include abdominal pain, nausea, vomiting, diarrhea, chills, hot flashes, restlessness, insomnia, general aches and pains, hypertension, anorexia, malaise, tachycardia, lacrimation, rhinorrhea, diaphoresis, and piloerection as well as a severe craving for the withdrawn target agent. Thus, administering a noncompetitive agent, in an amount sufficient to block the autonomic nervous system, blocks the major symptoms of withdrawal, without the activation of the target agent binding sites.

Next, the subject is administered a short acting high affinity competitive therapeutic agent, in an amount effective to reduce physiological levels of target agent in said subject. During this period, the short acting high affinity competitive therapeutic agent displaces the target agent from the binding sites; therefore, the physiological level of unbound target agent increases and consequently its elimination also increases. Consequently, the physiological level, of the target agent, is reduced.

The subject is then administered a long acting moderate affinity competitive therapeutic agent, that is also a partial agonist. The considerations that determine when the long acting moderate affinity competitive therapeutic agent is administered are, as discussed above, the affinity and half life of the short acting competitive therapeutic agent, and the withdrawal symptoms exhibited by the patient.

More specifically, the half life and affinity of the short acting competitive therapeutic agent are important, because it is one of the purposes of the long acting moderate affinity competitive inhibitor to compete with the unbound target agent for the binding cites, as they are vacated by the short acting competitive therapeutic agent. Therefore, the weaker the affinity and the shorter the half life of the first competitive therapeutic agent, the sooner the second competitive therapeutic agent must be administered to ensure that the target agent does not rebind to the binding sites.

Moreover, this second consideration—i.e. the withdrawal symptons exhibited by the subject—is also important because the long acting moderate affinity competitive agent also exhibits agonistic properties that are similar to those of the target agent. Therefore, the long acting moderate affinity competitive agent will decrease the withdrawal symptoms associated with the reduction in the physiological levels of the target agent; such symptoms which are brought on by the short acting high affinity competitive agent, but are not inhibited by the autonomic nervous system blocker.

The elimination phase involves a period wherein a long acting moderate affinity competitive therapeutic agent is administered. As its name implies, the elimination phase is designed to facilitate the substantial elimination of the addictive agent from the patient.

The elimination phase is facilitated by the administration of a competitive therapeutic agent that is an agonist-antagonist of the target agent. The competitive therapeutic agent is administered in amounts effective to inhibit the rebinding of the target agent, thereby facilitating the reduction of the physiological level of the target agent. Moreover, the therapeutic agent is administered in amounts effective to moderate the withdrawal symptoms associated with the reduction of the physiological level of the target agent.

The second induction phase involves the determination of the physiological level of the target agent, and the proper hydration of the patient. During the second induction phase, there should be little if any bound or unbound physiological level of target agent left in the patient.

As in the first induction phase, determination of such target agent physiological level is followed by administration of an autonomic nervous system blocker. The autonomic nervous system blocker is administered in amounts effective to block the autonomic nervous system.

The next successive therapeutic agent administered to the subject, in the second induction phase, is a short acting high affinity competitive agent that is an antagonist of the target agent. The short acting high affinity competitive antagonist is administered in amounts effective to displace the agonist-antagonist from the target agent binding sites.

The next successive therapeutic agent administered to the subject is a long acting competitive antagonist of the target agent. The long acting competitive antagonist of the target agent is administered in amounts effective to displace the short acting high affinity competitive antagonist from the target agent binding sites.

The subject is then administered an agonist-antagonist in an amount effective to control any symptoms associated with the administration of the short acting high affinity competitive antagonist.

The major difference between the first and second induction phases is that, during the second induction phase, the physiological level of long acting competitive antagonist is increased, such that by the end of the second induction phase, the long acting competitive antagonist fails to evoke withdrawal symptoms in the subject; specifically, the subject is administered a long acting competitive antagonist in an amount effective to substantiate that the subject is no longer addicted to the target agent.

It is further preferred that in the practice of the present invention, an initial urinalysis is conducted on the subject's urine. This urinalysis serves various functions, one such function being to evaluate the initial physiological level of target agent in the subject and to indicate how much target agent must be eliminated for the subject to be detoxified.

A particularly preferred embodiment of this present invention, involves treatment of heroin as the target agent; in such instance, the initial urinalysis determines the initial physiological level of heroin in the subject. This initial physiological level of heroin is an indication of the amount of heroin that must be eliminated from the subject.

The initial urinalysis serves a further function in the embodiment of the invention wherein the target agent is heroin. In this embodiment, the initial urinalysis also provides information as to whether a process of this present invention is suitable for the intended subject.

More specifically, the therapeutic agents used to reduce the physiological level of heroin, produce adverse reactions in subjects who have physiological levels of methadone. Therefore, the initial urinalysis is used to screen out subjects who have had an administration of methadone within the preceding 30 days. Therefore, the initial urinalysis not only gives an indication of the concentration of heroin, but also alerts the practitioners of the invention that a potential subject may be an unacceptable candidate for the invention.

Furthermore, in a preferred embodiment, the invention calls for periodic urinalysis through out the withdrawal period. This periodic urinalysis is important for the following reasons: firstly, it provides a measure of the effectiveness of the invention; secondly, it provides the signal when the different phases of treatment can begin; and thirdly, it provides the information as to whether the subject is following the treatment or whether the subject should be discontinued from the invention because he or she is returning to the self administration of the target agent.

Concerning the use of urinalysis to judge the effectiveness of the process of this present invention, in treating heroin as the target agent, urinalysis should indicate that there is a substantial drop in the level of systemic heroin after the initial induction. For example, the initial urinalysis may be 18,000 nanograms/deciliter of heroin, and after the threshold induction, the level should probably drop to approximately 10 to 12 nanograms/deciliter.

This change in urinary heroin level indicates that the invention is being effective for its intended purpose, and furthermore indicates whether the subject is following the treatment. For example, a smaller drop in the urinary heroin level might indicate that the subject has not completely stopped the self administration of heroin, and further may indicate that the subject is not a satisfactory candidate for the invention.

In large part, the process of this present invention is discussed hereinafter with reference to the treatment of heroin as the target agent, though the invention is also discussed more generally. However, it is specifically understood that the invention is not limited to treatment of heroin, but, rather, applies to all target agents for which the present invention has utility, in view of its stated purpose—i.e., treatment of addiction. For instance, specific target agents with which the present invention can be practiced—particularly, in the embodiment as hereinafter discussed—include all manner of opioids, such as demerol, dilaudid, and codeine, in addition to the indicated heroin, as well as two or more of such opioids in combination.

Specifically, the first induction phase begins on the day following the initial urinalysis. The subject is instructed to discontinue the self administration of heroin on the day the initial urinalysis is conducted.

The first induction phase is best initiated when the subject is beginning to feel the first stages of withdrawal. A second urinalysis is carried out on the subject's urine before the first induction phase is begun.

The first induction phase begins with the intravenous administration of 1000 cc. of 5% dextrose and water (D5W), normal saline, or an other comparable hydration fluid, by intravenous line. The hydration step is carried out in order to ensure that the blood volume of the subject is at an adequate level to promote urination—specifically, many target agents including heroin, are eliminated, when they are in the unbound form, through the urine; this hydration step ensures that such elimination will take place at a high rate.

Next, the subject is administered an autonomic nervous system blocker. As previously discussed, this agent provides supplementary symptom control during periods of time when the competitive agent does not adequately provide such activity.

Specifically, the subject is administered 50 to 100 mg. hydroxyzine hydrochloride by mouth and another 50 to 100 mg. by slow intravenous push. The amount of hydroxyzine hydrochloride administered depends on the patient's weight and age.

Following the administration of such autonomic nervous system blocker, a period of time is allotted for this therapeutic agent to block the autonomic nervous system. For the indicated administration of hydroxyzine hydrochloride, the period of time necessary for this therapeutic agent to take effect is approximately 20 to 40 minutes, and this is usually accompanied by the subject exhibiting a dry mouth.

The next therapeutic agent administered is the short acting competitive antagonist, in an amount effective to substantially eliminate the target agent. This therapeutic agent substantially displaces the target agent by successfully competing with the target agent for binding sites.

In this instance—i.e., for treating heroin as the target agent—the short acting competitive antagonist is preferably naloxone. The amount of naloxone administered to the subject is approximately 0.2 to 2.0 mg., by intravenous push.

The subject will begin to feel mild symptoms of withdrawal as the target agent—i.e., heroin—is displaced from the receptors and replaced with an antagonist—i.e., naloxone; specifically, although the autonomic nervous system is being blocked, other symptoms, such as anxiety and craving, are not blocked. Yet further, if there is any physiological level of methadone in the subject, the withdrawal symptoms will be very severe, and even worse if there is cocaine present.

The subject is allowed to remain in this state, for about 20 to 40 minutes to provide the time necessary for the subject to excrete unbound heroin. At the end of this time period, the subject will generally experience a bowel movement, which is indicative of the end of this stage.

Next, the subject is administered a selective agonist-antagonist—preferably, in treating heroin as the target agent, buprenorphine; in this stage, the selective agonist-antagonist has the dual function of competing with remaining target agent for binding sites, and affecting withdrawal symptoms. Preferably, the buprenorphine is administered in the amount of about 0.3 to 2.1 mg. by intramuscular injection.

The first induction phase concludes when the symptoms of withdrawal are moderated by the agonist-antagonist. Specifically, for buprenorphine, the first induction phase ends in approximately 5 to 15 minutes after the administration of the buprenorphine—i.e., when the subject usually experiences a feeling of well-being, due to the activity of the buprenorphine.

The elimination phase begins at the conclusion of the first induction phase. During this period, the physiological level of the target agent is being reduced, due to competition with the selective agonist-antagonist for binding sites.

Moreover, the elimination phase is a period during which the symptoms of withdrawal are being controlled by the selective agonist-antagonist. Where, as indicated, the selective agonist-antagonist is buprenorphine, the elimination phase lasts approximately 72 hours. Moreover, preferably, the buprenorphine is administered in intramuscular injections of approximately 0.3 to 2.1 mg, approximately every 8-12 hours.

Periodically, throughout the elimination phase, urinalysis of the subject's urine is carried out. As discussed above, urinalysis serves a number of purposes, not the least of which is to determine when the physiological level of the target agent is eliminated.

Specifically, where heroin is the target agent, urinalysis is carried out approximately every 12 hours. Moreover, at the end of the elimination phase, urinalysis should indicate the presence of no detectable heroin.

In the event that urinalysis indicates that there is an increase in the heroin level, the subject is reevaluated. If the subject recommits to withdrawing from addiction, the subject is returned to the beginning of the first induction phase, and the process is repeated.

The second induction phase begins when the urinalysis indicates that there is no longer any physiological level of target agent in the subject. For heroin, the physiological level should be negligible approximately 72 hours after the start of the elimination phase, or 8-12 hours after the last intramuscular administration of buprenorphine.

The second induction phase begins, as did the first induction phase, with the hydration of the subject. This is accomplished, for example, as before, with the placing of an intravenous line of 1000 cc., of 5% dextrose and water (D5W), normal saline, or some comparable fluid.

The subject is then administered an autonomic nervous system blocker, followed by a short acting competitive antagonist. The administration of the short acting competitive antagonist should replace substantially all other competitive agents on the opioid receptors.

In treating heroin as the target agent, antihistamines, such as the hydroxyzines, are suitable autonomic nervous system blockers. Specifically, the subject is orally administered 50 to 100 mg hydroxyzine pamoate, followed, in 2 to 10 minutes, with the administration of 50 to 100 mg hydroxyzine hydrochloride by intravenous push. The effective amount administered of either hydroxyzine pamoate or hydroxyzine hydrochloride is dependent upon the patient weight and age.

The hydroxyzine will take effect in about 20 to 40 minutes, with the patient developing a "dry mouth".

Further in treating heroin as the target agent, the preferred short acting high affinity competitive antagonist is naloxone. Specifically, within approximately, 20 40 minutes after the administration of the hydroxyzine hydrochloride, the subject is administered 0.2 to 2.0 mg, of naloxone by intravenous push.

Approximately 2 hours after the administration of the short acting antagonist, the subject is administered a long acting antagonist followed by an selective agonist-antagonist. The first administration of the long acting antagonist begins the process of substantiating that the subject is no longer addicted to the target agent.

In treating heroin as the target agent, the long acting antagonist is preferably naltrexone, and the selective agonist-antagonist is preferably buprenorphine. The naltrexone is orally administered, in a dosage of approximately 12.5 mg.; this dose of naltrexone is followed in approximately 2-3 minutes, with an intramuscular injection of approximately 0.3-0.6 mg. of buprenorphine.

12 hours after the last administration of buprenorphine, the subject is again orally administered 12.5 mg. of naltrexone. The administration of naltrexone is again followed by the intramuscular administration of 0.3-0.6 mg. of buprenorphine.

12 hours after the administration of the indicated dosage of buprenorphine, the subject is orally administered 25 mg. of naltrexone. The administration of naltrexone is again followed by the intramuscular administration of 0.3-0.6 mg. of buprenorphine.

12 hours after the administration of the last dosage of buprenorphine, the subject is orally administered 50 mg. of naltrexone. Tolerance of this dosage—more specifically, the failure of this dosage to evoke withdrawal symptoms—confirms that the subject is no longer addicted to heroin.

Successful completion of a withdrawal protocol—i.e., for removing the addiction—does not necessarily guarantee that the subject will not revert to use of the addictive agent; it is well known in the art that previously addicted subjects are vulnerable to readdiction. For this reason, it is customary, following the conclusion of withdrawal therapy, to employ a maintenance program to prevent readdiction.

The method of the invention, in itself, will be sufficient to prevent such readdiction—in at least some subjects—without a maintenance program being required. However, it is further contemplated that the method of the invention, in the same manner as the withdrawal treatment known in the art, will also be conducted in conjunction with a maintenance program—preferably of extended duration.

An appropriate maintenance program, contemplated for practice in conjunction with the method of the invention, utilizes administration of the long acting competitive antagonist at regular intervals, for an extended period of time. Particularly in the context of heroin addiction, administration of approximately 150 mg. of naltrexone, every 3 to 4 days, for a period of 3 to 6 months, may be suitable.

The exact dosages, and intervals of administration, will depend upon a variety of factors, including the sex, size, age and weight of the subject, and the susceptibility of the particular subject to the addictive agent. Such dosages and intervals of administration can be readily determined by those of ordinary skill in the art, without undue experimentation.

Successful maintenance programs further generally incorporate suitable counseling. Employment of such counseling, in conjunction with the indicated administration of a long acting competitive antagonist, is also contemplated in conjunction with the method of the invention.

Although the invention has been described with references to particular means, materials and embodiments, it is to be understood that the invention is not limited to the particulars disclosed and extends to all equivalents within the scope of the claims.

What is claimed is:

1. A method of treating addiction of a subject to heroin, comprising:
   (1) conducting urinalysis of said subject's urine, to determine base line physiological level of heroin in said subject;
   (2) administering approximately 1000 cc. of a medium, comprising 5% dextrose and water, normal saline solution, lactated ringer's solution, or sterile water to said subject;
   (3) administering approximately 50-100 mg. hydroxyzine, and further separately administering another approximately 50-100 mg. hydroxyzine, to said subject;
   (4) after approximately 20-40 minutes, administering approximately 0.2-2.0 mg. naloxone to said subject;
   (5) after approximately 20-30 minutes, administering approximately 0.3-2.1 mg. buprenorphine to said subject;
   (6) after approximately 8-12 hours, administering approximately 0.3-2.1 mg buprenorphine to said subject;
   (7) repeating step (6) approximately 6-9 times, during a period of approximately 72 hours:
   (8) conducting urinalysis of the subject's urine, every 12 hours during step (7), to determine the physiological level of heroin in said subject;
   (9) administering approximately 1000 cc. of a medium comprising 5% dextrose and water, normal saline solution, lactated ringer's solution, or sterile water to said subject;
   (10) administering approximately 100-200 mg of hydroxyzine to the subject;
   (11) after approximately 20-40 minutes, administering approximately 0.2-2.0 mg. naloxone to said subject;
   (12) after approximately 2 hours, administering 12.5 mg of naltrexone to said subject;
   (13) after approximately 2-3 minutes, administering approximately 0.3-0.6 mg. of buprenorphine to said subject;
   (14) after approximately 12 hours, repeating steps (12) and (13);
   (15) after approximately 12 hours, administering approximately 25 mg. of naltrexone to said subject;
   (16) repeating step (13); and
   (17) after approximately 12 hours, administering approximately 50 mg. of naltrexone to said subject;

* * * * *